United States Patent [19]

Janssen et al.

[11] Patent Number: 4,723,042
[45] Date of Patent: Feb. 2, 1988

[54] ALPHA,BETA-SUBSTITUTED ACROLEINS AND THEIR PREPARATION

[75] Inventors: Bernd Janssen; Stefan Karbach; Hans-Gert Recker; Marco Thyes, all of Ludwigshafen, Fed. Rep. of Germany

[73] Assignee: BASF Aktiengesellschaft, Ludwigshafen, Fed. Rep. of Germany

[21] Appl. No.: 5,691

[22] Filed: Jan. 22, 1987

[30] Foreign Application Priority Data

Jan. 23, 1986 [DE] Fed. Rep. of Germany ....... 3601927

[51] Int. Cl.$^4$ ............................................. C07C 45/00
[52] U.S. Cl. ................................... 568/433; 568/426; 568/440
[58] Field of Search ................ 568/426, 433, 437, 440

[56] References Cited

U.S. PATENT DOCUMENTS 2,628,255  2/1953  Sexton et al. ...................... 568/427
3,344,191  9/1967  Chappell et al. ................... 568/427

OTHER PUBLICATIONS

Methoden Der Organischen Chemie (Houben-Weyl), VI/3, pp. 371-372 (1965).
Journal of Organic Chemistry, vol. 30, pp. 2074-2075 (1965).
Journal of the American Chemical Society, vol. 95, No. 17, pp. 6136-6137 (1973).
Journal of the American Chemical Society, vol. 102, pp. 5974-5980 (1980).
Annalen der Chemie, vol. 596, pp. 128-129 (1955).
H. E. Zimmerman, L. Singer und B. S. Thyagarajan, "Overlap Control of Carbanionoid Reactions-Stereoselectivity in Alkaline Epoxidation," Jl. of Am. Chem. Soc. 81, 108-116 (1959).
K. Alder, J. Hayden, K. Heimbach and K. Neufang, "Darstellung Einiger 1,2-Disubstituieter Diene und Ihre Verwendung zn Dien-Synthesen," *Annalen der Chemie*, vol. 586, pp. 110-136 (1954).

*Primary Examiner*—Werren B. Lone
*Attorney, Agent, or Firm*—Keil & Weinkauf

[57] ABSTRACT

Alpha,beta-substituted acroleins of the general formula I

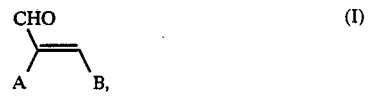

where A and B are identical or different and are each $C_1$–$C_4$-alkyl, naphthyl, biphenyl or phenyl which may be monosubstituted or polysubstituted by halogen, nitro, $C_1$–$C_4$-alkyl, $C_1$–$C_4$-alkoxy, $C_1$–$C_4$-haloalkyl, phenoxy or phenylsulfonyl, are prepared by a process in which a compound of the general formula III

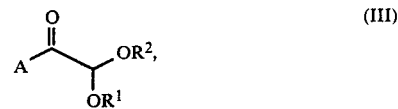

where A has the above meanings and $R^1$ and $R^2$ are identical or different and are each $C_1$–$C_4$-alkyl or together possess the carbon atoms required to complete a ring, is reacted with a phosphorus compound of the general formula IV or V

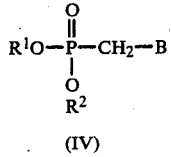 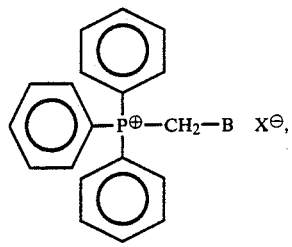

where B the meanings stated above, $R^1$ and $R^2$ are as defined above and $X^\ominus$ is a halide ion, in the presence of a base. The alpha,beta-substituted acroleins can be further processed to give hydroxymethyloxiranes.

5 Claims, No Drawings

ALPHA,BETA-SUBSTITUTED ACROLEINS AND THEIR PREPARATION

The present invention relates t alpha,beta-substituted acroleins, a process for their preparation, and their use for the preparation of hydroxymethyloxiranes.

Hydroxymethyloxiranes are useful intermediates for the synthesis of antimycotic and fungicidal azolylmethyloxiranes, which are described in European Patent Application No. 94,564 of the Applicant. These compounds can be prepared by reacting halomethyloxiranes, obtainable from hydroxymethyloxiranes, with the appropriate triazoles or amidazoles or the reactive derivatives of these compounds. According to EP-A-94 564, the hydroxymethyloxiranes can be prepared by epoxidation of the corresponding allyl alcohols.

The preparation of hydroxymethyloxiranes by epoxidation of the corresponding allyl alcohols is also described in other publications, for example in HoubenWeyl, VI/3, 371, in J. Org. Chem. 30 (1965), 2074, and in J. Am. Chem. Soc. 102 (1980), 5974 and ibid. 95 (1973), 6136.

The disadvantage of the known processes is that exposure to heat frequently leads to E/Z isomer mixtures during the epoxidation. Moreover, some of the appropriate allyl alcohols are very difficult to obtain.

It is an object of the present invention to provide novel alpha,beta-substituted acroleins from which hydroxymethyloxiranes can be prepared stereoselectively and in very high yields, and a process for the preparation of the said acroleins.

We have found that this object is achieved by providing alpha,beta-substituted acroleins of the general formula I

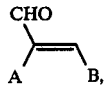

where A and B are identical or different and are each $C_1$–$C_4$-alkyl, naphthyl, biphenyl or phenyl which may be monosubstituted or polysubstituted by halogen, nitro, $C_1$–$C_4$-alkyl, $C_1$–$C_4$-alkoxy, $C_1$–$C_4$-haloalkyl, phenoxy or phenylsulfonyl.

In the process for the preparation of the alpha,beta-substituted acroleins of the general formula I, a compound of the general formula III

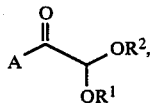

where A has the above meanings and $R^1$ and $R^2$ are identical or different and are each $C_1$–$C_4$-alkyl or together possess the carbon atoms required to complete a ring, is reacted with a phosphorus compound of the general formula IV or V

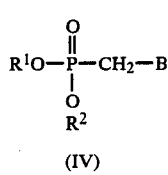 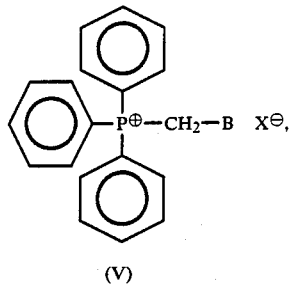

where B has the above meanings, $R^1$ and $R^2$ are as defined above and $X^-$ is a halide ion, in the presence of a base The novel alpha,beta-substituted acroleins are further processed by epoxidizing them to give the corresponding formyloxiranes and reducing the latter directly in the reaction mixture, i.e. in a one-vessel reaction, to give the hydroxymethyloxiranes of the formula II

where A and B have the above meanings.

We have found, surprisingly, that the novel alpha,-beta-substituted acroleins can be converted to the hydroxymethyloxiranes in very high yields, some of these compounds being formed stereoselectively.

The conversion of the novel alpha,beta-substituted acroleins to the methyloxiranes is effected, if desired, in the presence of a solvent or diluent and, if desired, with the addition of an organic or inorganic base as a catalyst.

The preferred solvents include alcohols, e.g. methanol, ethanol, isopropanol, n-propanol, n-butanol, isobutanol, tert.-butanol or cyclohexanol, halohydrocarbons, e.g. methylene chloride, chloroform, carbon tetrachloride, dichloroethane or chlorobenzene, hydrocarbons, such as pentane, hexane, heptane, cyclohexane, toluene or xylene, and amides, e.g. dimethylacetamide or N-methyl-pyrrolidone. Other suitable solvents are nitriles, e.g. acetonitrile, and sulfoxides, e.g. dimethylsulfoxide. Urea derivatives, e.g. 1,3-dimethyl-3,4,5-tetrahydro-2 (1H)-pyrimidinone (DMPU), can also be used. Mixtures of these solvents may also be advantageously employed. If necessary, the reaction is carried out with the addition of a phase transfer catalyst, for example one of those described by E. V. Dehmlow and S. S. Dehmlow, Phase Transfer Catalysis (1980), Verlag Chemie.

Examples of suitable bases are alkali metal hydroxides, e.g. sodium hydroxide or potassium hydroxide, alkali metal carbonates, e.g. sodium carbonate or potassium carbonate, alcoholates, e.g. sodium or potassium methylate, ethylate, propylate, isopropylate, n-butylate, isobutylate, tert-butylate or cyclohexylate, and tertiary amines, e.g. trialkylamines, where the alkyl radicals are identical or different and may be methyl, ethyl, propyl, isopropyl, n-butyl, isobutyl, tert.-butyl or cyclohexyl. Aromatic amines, e.g. pyridine or N,N'-dimethylaminopyridine, may also be employed. Sodium hydroxide, potassium hydroxide, sodium carbonate and potassium carbonate are particularly preferred.

The basic catalyst is advantageously used for the reaction in an amount of, for example, from 0.1 to 20, preferably from 0.5 to 10, mol percent, based on the alpha,beta-substituted acrolein of the general formula II which is employed.

From 3 to 80, in particular from 20 to 60, particularly preferably 30, percent strength aqueous hydrogen peroxide solutions are suitable for the epoxidation.

Suitable reducing agents are metal hydrides, e.g. diisobutylaluminum hydride or sodium, lithium or potassium hydride, borohydride or cyanoborohydride, as well as lithium aluminum hydrides of the general formula $$Li\, Al\, (H)_m\, (OR)_n$$

where m is from 1 to 4, n is 4 - m and the radicals R may be identical or different and are each in general alkyl, e.g. methyl, ethyl, propyl, isopropyl, n-butyl, isobutyl, tert.-butyl or cyclohexyl, or hydrogen, in the presence or absence of a suitable catalyst, e.g. rhodium or ruthenium. Sodium borohydride is particularly preferred.

The reaction is carried out in general at from $-20°$ to $+120°$ C., preferably from $-5°$ to $+50°$ C., particularly preferably from $0°$ to $+33°$ C., under atmospheric or superatmospheric pressure, continuously or batchwise.

The epoxidation is carried out using, as a rule, equimolar amounts of the alpha,beta-substituted acrolein and $H_2O_2$. However, it is also possible to use an excess of $H_2O_2$, for example from 1 to 20%.

The reduction is preferably carried out using stoichiometric amounts of the reducing agent, although it is also possible to employ an excess, e.g. 0.5–20%.

When the reaction is complete, the end product can be isolated in a conventional manner, for example by extraction with a suitable organic solvent, e.g. a chlorohydrocarbon, hydrocarbon, ester or ether, or particularly preferably by direct crystallization from the reaction mixture, if necessary by adding water.

The rapid and virtually quantitative conversion of the alpha,beta-substituted acroleins of the general formula II to the hydroxymethyloxiranes of the general formula I is surprising in that the epoxyaldehydes formed as intermediates are very unstable and readily react further to give the corresponding acids or cleavage products as a result of opening of the oxirane ring.

However, the one-stage procedure described for the use according to the invention makes it possible to dispense with isolation of these labile intermediates. In a technically advantageous version of this process, the working-up step is substantially simplified in that an extraction and purification procedure can be dispensed with since in general the end product crystallizes out directly from the reaction mixture.

In the compounds of the general formulae I and II, the radicals A and B are each preferably methyl, ethyl, propyl, isopropyl, butyl, sec.-butyl, isobutyl, tert.-butyl, 1-naphthyl, 2-naphthyl, p-biphenyl, phenyl, 2-chlorophenyl, 3-chlorophenyl, 4-chlorophenyl, 2-fluorophenyl, 3-fluorophenyl, 2-fluoro-6-chlorophenyl, 4-fluorophenyl, 4-bromophenyl, 2,4-dichlorophenyl, 3,4-dichlorophenyl, 3,5-dichlorophenyl, 2,6-dichlorophenyl, 3-chloro-4-methylphenyl, 2-methoxyphenyl, 3-methoxyphenyl, 2,4-dimethoxyphenyl, 3,4-dimethoxyphenyl, 4-methoxyphenyl, 4-ethoxyphenyl, 4-tert.-butoxyphenyl, 4-methylphenyl, 4-ethylphenyl, 4-isopropylphenyl, 4-tert.-butylphenyl, 4-phenoxyphenyl, 3-phenoxyphenyl, 3-nitrophenyl, 4-nitrophenyl, 3-trifluoromethylphenyl, 4-trifluoromethylphenyl or 4-phenylsulfonylphenyl.

A and B in the compounds of the general formulae I and II are each particularly preferably methyl, tert.-butyl, phenyl, 2-chlorophenyl, 4-chlorophenyl, 2-fluorophenyl, 3-fluorophenyl, 4-fluorophenyl, 2-fluoro-6-chlorophenyl, 4-bromophenyl, 2,4-dichlorophenyl or 4-tert.-butylphenyl.

The prior art discloses processes for the preparation of phenyl-substituted acroleins of the general formula I of the appropriate type, but these processes give poor yields.

For example, the condensation of phenylacetaldehyde, which is very difficult to handle, with benzaldehyde (in 15% excess) gives alpha-phenylcinnamaldehyde in a yield of only about 70% (Alder et al., Ann. Chem. 596 (1954), 128. Undefined product mixtures which are relatively difficult to separate are frequently formed, and these mixed aldol condensations are therefore of very little importance industrially (A. T. Nielsen and W. J. Houlihar, Org. Reactions 16 (1968); Houben-Weyl VII/1, 76). In particular, the synthesis of the acceptor-substituted alpha-phenylacroleins by this method is extremely unsatisfactory, since both the preparation and the handling of the corresponding acceptor-substituted phenylacetaldehydes are extremely difficult.

Furthermore, the reaction of cinnamaldehyde with aromatic diazonium salts, e.g. p-chlorobenzenediazonium chloride, to give alpha-phenyl-substituted cinnamaldehydes gives extremely unsatisfactory yields of about 35% (H. Meerwein et al., J. prakt. Chemie 152, 1935 and Org. Reactions 24 (1973), 225)

According to the invention, a process for the preparation of the alpha,beta-substituted acroleins of the general formula I is provided in which a compound of the general formula III

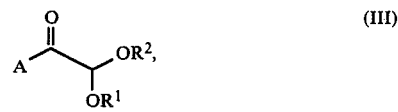
(III)

where A has the meanings stated in claims 1 to 3 and $R^1$ and $R^2$ are identical or different and are each $C_1$–$C_4$-alkyl or together possess the carbon atoms required to complete a ring, is reacted with a phosphorus compound of the general formula IV or V

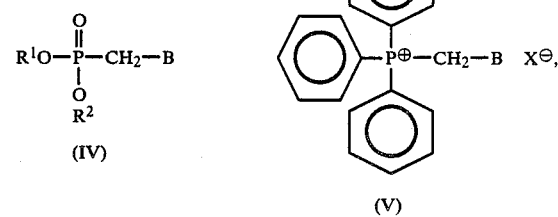

where P has the meanings stated in claims 1 to 3, $R^1$ and $R^2$ are as defined above and $X^\ominus$ is a halide ion, in the presence of a base.

This reaction gives very high yields and is in some cases stereoselective. The starting compounds of the general formula III are described in, for example, DE-A No. 34 07 005, and some of them in German Patent Application P No. 35 39 629.6 of the Applicant.

In the compounds of the general formulae III, IV and V, A and B have the same meanings as in the compounds of the general formulae I and II. A and B are each preferably methyl, ethyl, propyl, isopropyl, butyl, sec.-butyl, isobutyl, tert.-butyl, 1-naphthyl, 2-naphthyl, p-biphenyl, phenyl, 2-chlorophenyl, 3-chlorophenyl, 4-chlorophenyl, 2-fluorophenyl, 3-fluorophenyl, 2-fluoro-6-chlorophenyl, 4-fluorophenyl, 4-bromophenyl, 2,4-dichlorophenyl, 3,4-dichlorophenyl, 3,5-dichlorophenyl, 2,6-dichlorophenyl, 3-chloro-4-methylphenyl, 2-methoxyphenyl, 3-methoxyphenyl, 2,4-dimethoxyphenyl, 3,4-dimethoxyphenyl, 4-methoxyphenyl, 4-ethoxyphenyl, 4-tert.-butoxyphenyl, 4-methylphenyl, 4-ethylphenyl, 4-isopropylphenyl, 4-tert.-butylphenyl, 4-phenoxyphenyl, 3-phenoxyphenyl, 3-nitrophenyl, 4-nitrophenyl, 3-trifluoromethylphenyl, 4-trifluoromethylphenyl or 4-phenylsulfonylphenyl.

A and B are each particularly preferably methyl, tert.-butyl, phenyl, 2-chlorophenyl, 4-chlorophenyl, 2-fluorophenyl, 3-fluorophenyl, 4-fluorophenyl, 2-fluoro-6-chlorophenyl, 4-bromophenyl, 2,4-dichlorophenyl or 4-tert.-butylphenyl.

The process for the preparation of the novel alpha,-beta-substituted acroleins is carried out in the presence or absence of a solvent or diluent and particularly advantageously at from $-10°$ to $+130°$ C. in the presence of a base.

The preferred solvents include alcohols, e.g. methanol, ethanol, propanol, isopropanol, n-butanol, isobutanol, tert.-butanol and cyclohexanol, hydrocarbons, e.g. pentane, hexane, heptane, toluene, xylene or cyclohexane, halohydrocarbons, e.g. methylene chloride, chloroform, carbon tetrachloride, dichloroethane or chlorobenzene, and ethers, e.g. diethyl ether, methyl tert.-butyl ether, glycol dimethyl ether, glycol diethyl ether, dioxane and tetrahydrofuran. Polar aprotic solvents, e.g. dimethyl sulfoxide, hexamethylphosphorotriamide, acetonitrile, N-methylpyrrolidone, dimethylacetamide or 1,3-dimethyl-3,4,5-tetrahydro-2-(1H)-pyrimidinone (DMPU), are particularly preferred. Dimethylformamide is very particularly preferred.

The reaction is advantageously carried out at from $-10$ to $+130°$ C., preferably from 0 to 60° C., particularly preferably from 10° to $+30°$ C.

Examples of suitable bases are alkali metal hydrides, such as lithium hydride, sodium hydride or potassium hydride, alkali metal amides, such as sodium amide, potassium amide, or lithium diisopropylamide, as well as alkali metal alcoholates, such as sodium and potassium tert.-tuboxide, sodium and potassium methylate and ethylate and sodium-triphenylmethyl, potassium-triphenylmethyl, naphthalenelithium, naphthalenesodium and naphthalenepotassium.

The alkali metal alcoholates, particularly preferably sodium and potassium methylate, ethylate, tert.-butylate and isopropylate, are preferably used.

In carrying out the process, equimolar amounts of the ketone of the general formula III and of the phosphorus compound of the general formula IV or V are preferably used.

However, it is also possible to employ an excess of a reactant, for example of a cheap reactant, e.g. an excess of up to 30%.

To isolate the alpha,beta-substituted acroleins of the general formula II, an aqueous mineral acid, e.g. HCl or $H_2SO_4$, is usually added and the end product is, if required, extracted from the reaction mixture with a suitable solvent, e.g. a hydrocarbon, chlorohydrocarbon, ester, ketone or ether. The compound of the formula II is particularly preferably crystallized out directly from the reaction mixture, if necessary with the addition of water.

The starting compound of the general formula IV is usually obtained by reacting the corresponding halide with an alkyl phosphite (Houben-Weyl XII/1, 433, and G. M. Kosolapoff, Org. Reactions 6 (1951), 276). The phosphonates thus obtained can be employed in the Wittig-Horner reaction in pure form or as a crude product.

The phosphonium salts of the general formula V are obtainable by reacting triphenylphosphine with the corresponding halides (A. Maerckier, Org. Reactions 14, (1965), 270; G. Wittig, Angew. Chem. 68, (1956), 505 and Houben-Weyl V/2a, 185).

The omega,omega'-bisalkoxyketones of the general formula III are obtainable, for example, by reacting methylketones with sulfuryl chloride or other conventional chlorinating agents in a conventional manner to give omega-dichloroketones, subjecting the latter to chloride exchange with an alkali metal alcoholate in the appropriate alcohol as a solvent, and directly transacetalizing the product with a concentrated mineral acid, e.g. HCl (DE No. 34 07 005 A1).

The examples which follow illustrate the invention.

I. Preparation of the hydroxymethyloxiranes

EXAMPLE 1

1-hydroxymethyl-1-(4-chlorophenyl)-2-phenyloxirane 70 g of 30% strength $H_2O_2$ are added dropwise at 5°–10° C. to a solution of 121 g of (E)-alpha-(4-chlorophenyl)-cinnamaldehyde in 400 ml of methanol and 3 ml of 25% strength NaOH. When the addition is complete, the mixture is stirred for a further hour at room temperature, after which 4.625 g of $NaBH_4$ are added at 10°–20° C. Stirring is continued for an hour at room temperature, and 500 ml of $H_2O$ are added, after which 116 g (89.2%) of 1-hydroxymethyl-1-(4-chlorophenyl)-2-phenyloxirane of melting point 90°–96° C. crystallize.

EXAMPLE 2

(Z)-2-(4-chlorophenyl)-3-(2,4-dichlorophenyl)-2-(hydroxymethyl)-oxirane 13.5 g (0.043 mol) of (E)-2-(4-chlorophenyl-3-(2,4-dichlorophenyl)-acrolein are added to a mixture of 0.65 g (0.005 mole) of potassium carbonate and 65 ml of methanol. 4.5 ml (5.0 g; 0.044 mole) of a 30% strength solution of hydrogen peroxide in water are then added dropwise to the stirred mixture under nitrogen in the course of about 15 minutes at from 0° to 5° C. The suspension is stirred for a further 30 minutes under $N_2$ at from 0° to 5° C., and the temperature is allowed to increase to about 25° C., while stirring. 0.95 g (0.025 mole) of sodium borohydride is added to the stirred mixture in the course of about 10 minutes at from 20° to 30° C. Thereafter, stirring is continued for a further hour at about 25° C., after which 200 ml of distilled water are added. 13.3 g (0.040 mole; 93% of theory) of colorless crystals of melting point 122°–127° C. are obtained; according to the $^1$H-NMR spectrum, these are a mixture of the (Z) and (E) isomers in a ratio of about 85:15.

The said mixture of (Z)- and (E)-2-(chlorophenyl)-3-(2,4-dichlorophenyl)-2-(hydroxymethyl)-oxirane is recrystallized from 150 ml of a 9:1 methanol/distilled water mixture. 9.0 g (0.027 mole; 64%) of (Z)-2-(4-chlorophenyl)-3-(2,4-dichlorophenyl)-2-(hydroxymethyl)-oxirane of melting point 137°–140° C. are obtained.

II. Preparation of the alpha,beta-substituted acroleins

EXAMPLE 3

(E)-(4-chlorophenyl)-cinnamaldehyde

A mixture of 500 g of diethyl benzylphosphite and 428 g of omega,omega'-bismethoxy-4-chloroacetophenone is added dropwise to a cooled solution of 270 g of potassium tert.-butoxide in 2 l of dimethylformamide at 10°–20° C. When the addition is complete, 1 l of 2 N HCl is metered in at 10°–25° C., while cooling with ice. After half an hour, a further 4 l of ice water are added, and the precipitated solid is filtered off under suction. 480 g (99%) of (E)-alpha-(4-chlorophenyl)cinnamaldehyde of melting point 70°–75° C. are obtained.

EXAMPLE 4

(E)-2-(4-chlorophenyl)-3-(2,4-dichlorophenyl)-acrolein 214 g (1.00 mole) of p-chloro-omega,omega-dimethoxyacetophenone are added dropwise, in the course of ten minutes at from 20° to 24° C., to a stirred mixture of 1,000 ml of dimethylformamide and 216 g (1.20 moles) of a 30% strength solution of sodium methylate in methanol. When the dropwise addition is complete, 312 g (1.05 moles) of diethyl (2,4-dichlorobenzyl)-phosphate are added in the course of 30 minutes at from 20° to 30° C., with further stirring. Thereafter, stirring is continued for 3.5 hours at about 25° C., and 2 l of distilled water are then added to the reaction mixture. Stirring is continued for a further 30 minutes, after which the product is filtered off under suction, washed with distilled water and dried in a drying oven under reduced pressure at 50° C. to give 350 g (0.98 mole; 98% of theory) of (E)-2-(4-chlorophenyl)-1-(2,4-dichlorophenyl)-3,3-dimethoxyprop-1-ene in the form of pale yellowish crystals of melting point 87°–90° C.

Thereafter, a mixture of 1,000 ml of distilled water, 500 ml of methanol, 50 ml (59.7 g; 0.62 mole) of concentrated hydrochloric acid and 350 g (0.98 mole) of (E)-2-(4-chlorophenyl)-1-(2,4-dichlorophenyl)-3,3-dimethoxyprop-1-ene (I) is refluxed for 4 hours, while stirring. The mixture is cooled to room temperature and 1,000 ml of water are then added, while stirring. 300 g (0.96 mole; 98% of theory) of (E)-2-(4-chlorophenyl)-3-(2,4-dichlorophenyl)-acrolein are isolated in the form of pale yellowish crystals of melting point 106°–109° C.

EXAMPLES 5 TO 67

The compounds listed in the table below were prepared, or can be prepared, by methods similar to those described in Examples 1 to 4. The alcohols obtained in the form of an oil or resin were characterized in some cases via the corresponding tosylates.

TABLE

| Example No. | A | B | CHO / A=B | OH / A-O-B | O Tos / A-O-B |
|---|---|---|---|---|---|
| 5 | $C_6H_5$ | 2-F—$C_6H_4$ | Öl | Öl | 85–88° |
| 6 | " | 3-F—$C_6H_4$ | | | |
| 7 | " | 4-F—$C_6H_4$ | | | |
| 8 | " | 2-F, 6-Cl—$C_6H_3$ | | | |
| 9 | " | 2-Cl—$C_6H_4$ | | | |
| 10 | " | 4-Br—$C_6H_4$ | 170–173 | | |
| 11 | 4(Phenyl)-$C_6H_4$ | 2-Cl—$C_6H_4$ | 106–108 | 153–155 | 99 |
| 12 | 2,4-$Cl_2$—$C_6H_3$ | $C_6H_5$ | | | |
| 13 | " | 2-F—$C_6H_4$ | 85–84 | Resin | |
| 14 | " | 3-F—$C_6H_4$ | | | |
| 15 | " | 4-F—$C_6H_4$ | | | |
| 16 | " | 2-F, 6-Cl—$C_6H_3$ | | | |
| 17 | " | 2-Cl—$C_6H_4$ | | | |
| 18 | " | 3-Cl—$C_6H_4$ | | | |
| 19 | " | 4-Cl—$C_6H_4$ | | | |
| 20 | " | 2,4-$Cl_2$—$C_6H_3$ | | | |
| 21 | " | 2,6-$Cl_2$—$C_6H_3$ | | | |
| 22 | 2-Cl—$C_6H_4$ | $C_6H_5$ | | | |
| 23 | " | 2-F—$C_6H_4$ | Resin | | |
| 24 | " | 3-F—$C_6H_4$ | Resin | | |
| 25 | " | 4-F—$C_6H_4$ | Resin | | |
| 26 | " | 2-Cl—$C_6H_4$ | 87 | Resin | 128–130 |
| 27 | " | 3-Cl—$C_6H_4$ | Resin | | |
| 28 | " | 4-Cl—$C_6$—$H_4$ | | | |
| 29 | " | 2,4-$Cl_2$—$H_3$ | | | |
| 30 | " | 2,6-$Cl_2$—$C_6H_3$ | | | |
| 31 | " | 4-Br—$C_6H_4$ | | | |
| 32 | 2-F—$C_6H_4$ | $C_6H_5$ | | | |
| 33 | " | 2-F—$C_6H_4$ | | | |
| 34 | " | 3-F—$C_6H_4$ | | | |
| 35 | " | 4-F—$C_6H_4$ | | | |
| 36 | " | 2-Cl—$C_6H_4$ | 106–109 | | |
| 37 | " | 3-Cl—$C_6H_4$ | | | |
| 38 | " | 4-Cl—$C_6H_4$ | | | |
| 39 | " | 2,4-$Cl_2$—$C_6H_3$ | | | |
| 40 | 4-Br—$C_6H_4$ | 2-Cl—$C_6H_4$ | | | |
| 41 | 4-F—$C_6H_4$ | $C_6H_5$ | | | |
| 42 | " | 2-F—$C_6H_4$ | 89–92 | | |
| 43 | " | 3-F—$C_6H_4$ | | | |
| 44 | " | 4-F—$C_6H_4$ | | | |

TABLE-continued

| Example No. | A | B | CHO A=B | OH A—B (with O) | O Tos A—B (with O) |
|---|---|---|---|---|---|
| 45 | " | 2-F, 4-Cl—C₆H₅ | | | |
| 46 | " | 2-Cl—C₆H₄ | 85–88 | 103–105 | 104–105 |
| 47 | " | 3-Cl—C₆H₄ | | | |
| 48 | " | 4-Cl—C₆H₄ | | | |
| 49 | " | 2,4-Cl₂—C₆H₃ | 98–101 | 130 | 116–117 |
| 50 | " | 2,6-Cl₂—C₆H₃ | | | |
| 51 | " | 4-Br—C₆H₄ | | | |
| 52 | 4-CH₃—C₆H₄ | C₆H₅ | | | |
| 53 | | 2-F—C₆H₄ | 75–78 | 77–80 | |
| 54 | | 3-F—C₆H₄ | | | |
| 55 | | 4-F—C₆H₄ | | | |
| 56 | | 2-Cl—C₆H₄ | 92 | 100–103 | 87 |
| 57 | | 3-Cl—C₆H₄ | | | |
| 58 | | 4-Cl—C₆H₄ | | | |
| 59 | | 2,4-Cl₂—C₆H₃ | | | |
| 60 | 4-Br—C₆H₄ | 4-Br—C₆H₄ | | | |
| 61 | 3-Br, 4-F—C₆H₃ | 2-F—C₆H₄ | 81–84 | 65–67 | |
| 62 | " | 2-Cl—C₆H₄ | 125–128 | | 100–104 |
| 63 | 4-Br—C₆H₄ | 2-Cl—C₆H₄ | | | |
| 64 | " | 4-Br—C₆H₄ | | | |
| 65 | 4-Cl—C₆H₄ | 2-F—C₆H₄ | 80–83 | 90–92 | |
| 66 | " | 2-F, 6-Cl—C₆H₃ | | | |
| 67 | " | 2-Cl—C₆H₄ | | | |

We claim:

1. A process for the preparation of an alpha,beta substituted acrolein of the formula I

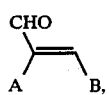
(I)

where A and B are identical or different and are each C₁-C₄-alkyl, naphtyl, biphenyl or phenyl which may be monosubstituted or polysubstituted by halogen, nitro, C₁-C₄-alkyl, C₁-C₄-alkoxy, C₁-C₄-haloalkyl, phenoxy or phenylsulfonyl which process comprises:

reacting a compound of the formula III

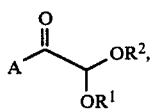
(III)

where A has the above meanings and R¹ and R² are identical or different and are each C₁-C₄-alkyl or together possess the carbon atoms required to completa a ring, with a phosphorus compound of the formula IV or V

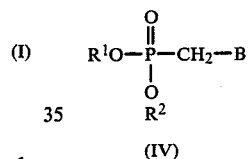
(IV)

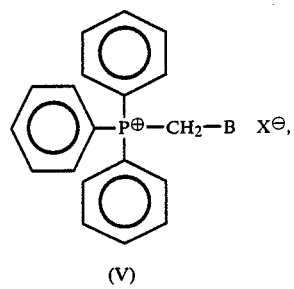
(V)

where B has the meanings stated above, R¹ and R² are as defined above and X⊖ is a halide ion, in the presence of a base.

2. The process of claim 1, wherein the reaction is carried out in a solvent or diluent at from −10° to +130° C.

3. The process of claim 1, wherein the reaction is carried out in a polar, aprotic solvent at from +10° to +30° C.

4. The process of claim 1, wherein A and B are defined as set forth in claim 2.

5. The process of claim 1, wherein A and B are defined as set forth in claim 3.

* * * * *